United States Patent
Webb et al.

(10) Patent No.: US 11,633,294 B2
(45) Date of Patent: Apr. 25, 2023

(54) ORTHOPAEDIC SURGICAL INSTRUMENT SYSTEM HAVING AN ANTERIOR-LOADING TIBIAL BEARING TRIAL AND ASSOCIATED SURGICAL METHOD OF USING THE SAME

(71) Applicant: DePuy Ireland Unlimited Company, Ringaskiddy (IE)

(72) Inventors: Anthony J. Webb, Fort Wayne, IN (US); Cory A. Shulaw, Warsaw, IN (US); Adam L. Carver, Raleigh, NC (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 284 days.

(21) Appl. No.: 16/707,425

(22) Filed: Dec. 9, 2019

(65) Prior Publication Data

US 2021/0169664 A1 Jun. 10, 2021

(51) Int. Cl.
  *A61F 2/46* (2006.01)
  *A61F 2/38* (2006.01)
  *A61F 2/30* (2006.01)

(52) U.S. Cl.
  CPC ............ *A61F 2/4684* (2013.01); *A61F 2/389* (2013.01); *A61F 2002/30331* (2013.01)

(58) Field of Classification Search
  CPC ...... A61F 2/3868; A61F 2/3886; A61F 2/389; A61F 2/4684; A61F 2002/305; A61F 2002/30607; A61F 2002/30428; A61F 2002/30479
  See application file for complete search history.

(56) References Cited

U.S. PATENT DOCUMENTS

| | | | |
|---|---|---|---|
| 5,879,394 A * | 3/1999 | Ashby | A61F 2/389 623/20.33 |
| 5,989,261 A | 11/1999 | Walker et al. | |
| 6,126,692 A * | 10/2000 | Robie | A61F 2/389 623/20.32 |
| 6,217,618 B1 * | 4/2001 | Hileman | A61F 2/3868 623/20.29 |
| 6,916,324 B2 | 7/2005 | Sanford et al. | |
| 7,628,818 B2 * | 12/2009 | Hazebrouck | A61F 2/389 623/20.14 |
| 7,691,150 B2 | 4/2010 | Cronin et al. | |
| 7,850,698 B2 | 12/2010 | Straszheim-Morley et al. | |
| 8,128,703 B2 * | 3/2012 | Hazebrouck | A61F 2/389 623/20.14 |
| 8,506,645 B2 | 8/2013 | Blaylock et al. | |

(Continued)

FOREIGN PATENT DOCUMENTS

EP 1186277 A2 3/2002
EP 2651327 A1 10/2013

(Continued)

OTHER PUBLICATIONS

Extended European Search Report for Application No. 20212564. 7-1122, dated Apr. 20, 2021, 6 pages.

*Primary Examiner* — Anu Ramana
(74) *Attorney, Agent, or Firm* — Barnes & Thornburg LLP (57) ABSTRACT

An orthopaedic surgical instrument system includes a tibial base trial and a tibial bearing trial. The tibial bearing trial is installed on the tibial base trial from the anterior side of the patient's tibia during an orthopaedic surgical procedure.

17 Claims, 7 Drawing Sheets

(56) References Cited

U.S. PATENT DOCUMENTS

| | | |
|---|---|---|
| 8,603,101 B2 | 12/2013 | Claypool et al. |
| 8,764,840 B2* | 7/2014 | Sanford .............. A61F 2/3836 623/20.28 |
| 8,986,310 B2 | 3/2015 | Bailey et al. |
| 9,011,459 B2 | 4/2015 | Claypool et al. |
| 9,149,206 B2 | 10/2015 | Claypool et al. |
| 9,265,614 B2 | 2/2016 | Blaylock et al. |
| 9,283,082 B2* | 3/2016 | Sanford .............. A61F 2/3836 |
| 9,427,337 B2 | 8/2016 | Claypool et al. |
| 9,492,178 B2 | 11/2016 | Neal et al. |
| 9,539,116 B2 | 1/2017 | Claypool et al. |
| 9,597,090 B2 | 3/2017 | Claypool et al. |
| 9,763,794 B2* | 9/2017 | Sanford .............. A61F 2/389 |
| 9,763,807 B2 | 9/2017 | Claypool et al. |
| 9,814,584 B2* | 11/2017 | Meier .............. A61F 2/389 |
| 9,907,664 B2 | 3/2018 | Blaylock et al. |
| 9,918,844 B2* | 3/2018 | Sanford .............. A61F 2/3836 |
| 9,925,052 B2 | 3/2018 | Dai et al. |
| 10,010,330 B2 | 7/2018 | Claypool et al. |
| 10,543,099 B2* | 1/2020 | Sanford .............. A61F 2/3836 |
| 2004/0162619 A1 | 8/2004 | Blaylock et al. |
| 2006/0184176 A1 | 8/2006 | Straszheim-Morley et al. |
| 2008/0051908 A1* | 2/2008 | Angibaud .............. A61F 2/389 623/20.32 |
| 2008/0147203 A1 | 6/2008 | Cronin et al. |
| 2010/0010635 A1 | 1/2010 | Straszheim-Morley et al. |
| 2010/0191342 A1 | 7/2010 | Byrd et al. |
| 2011/0009974 A1 | 1/2011 | Blaylock et al. |
| 2011/0218541 A1 | 9/2011 | Bailey et al. |
| 2012/0158152 A1 | 6/2012 | Claypool et al. |
| 2012/0323334 A1 | 12/2012 | Jones et al. |
| 2013/0006378 A1* | 1/2013 | Wogoman .............. A61F 2/3859 623/20.35 |
| 2013/0253378 A1 | 9/2013 | Claypool et al. |
| 2013/0261504 A1 | 10/2013 | Claypool et al. |
| 2013/0261757 A1 | 10/2013 | Claypool et al. |
| 2013/0261759 A1 | 10/2013 | Claypool et al. |
| 2013/0304221 A1 | 11/2013 | Blaylock et al. |
| 2014/0052269 A1 | 2/2014 | Claypool et al. |
| 2014/0288564 A1 | 9/2014 | Bailey et al. |
| 2015/0190243 A1 | 7/2015 | Claypool et al. |
| 2015/0359642 A1 | 12/2015 | Claypool et al. |
| 2016/0128701 A1 | 5/2016 | Neal et al. |
| 2016/0324647 A1 | 11/2016 | Claypool et al. |
| 2017/0049582 A1 | 2/2017 | Braun et al. |
| 2017/0156736 A1 | 6/2017 | Claypool et al. |
| 2018/0000612 A1 | 1/2018 | Claypool et al. |
| 2018/0098856 A1 | 4/2018 | Blaylock et al. |
| 2018/0103966 A1 | 4/2018 | Jones et al. |

FOREIGN PATENT DOCUMENTS

| | | |
|---|---|---|
| EP | 2939615 A1 | 11/2015 |
| EP | 2849684 B1 | 5/2016 |
| EP | 2918235 B1 | 1/2017 |
| EP | 2651343 B1 | 3/2017 |
| EP | 2720649 B1 | 4/2017 |
| EP | 2830543 B1 | 11/2017 |
| EP | 3335674 A2 | 6/2018 |
| EP | 3545911 A1 | 10/2019 |
| WO | 2006088684 A1 | 8/2006 |
| WO | 2010088229 A2 | 8/2010 |
| WO | 2012082628 A1 | 6/2012 |
| WO | 2012083280 A1 | 6/2012 |
| WO | 2012173740 A1 | 12/2012 |
| WO | 2018071693 A1 | 4/2018 |

\* cited by examiner

ORTHOPAEDIC SURGICAL INSTRUMENT SYSTEM HAVING AN ANTERIOR-LOADING TIBIAL BEARING TRIAL AND ASSOCIATED SURGICAL METHOD OF USING THE SAME

TECHNICAL FIELD

The present disclosure relates generally to orthopaedic surgical instruments, and particularly to a tibial bearing trial for use in trialing an orthopaedic knee prosthesis.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. In a revision knee surgery, the previously-implanted knee prosthesis, sometimes referred to as a "primary knee prosthesis," is surgically removed and a replacement or revision knee prosthesis is implanted. A typical knee prosthesis includes a tibial tray, a femoral component, and a polymer bearing (also known as an "insert") positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur During joint arthroplasty, trial components may be used to size and select the components of the knee prosthesis that will replace the patient's natural joint. Trial components may include a femoral trial that may be used to size and select a prosthetic femoral component, a tibial tray trial that may be used to size and select a prosthetic tibial tray, and a tibial bearing trial that may be used to size and select a prosthetic tibial bearing.

SUMMARY

According to an aspect of the disclosure, an orthopaedic surgical instrument system includes a tibial bearing trial that has an inferior surface and a superior surface opposite the inferior surface. A pair of curved bearing surfaces are formed in the superior surface. The tibial bearing trial also has a sidewall extending between the inferior surface and the superior surface. A channel is formed in the inferior surface. A posterior end of the channel is defined by an opening formed in a posterior section of the sidewall. An anterior end of the channel is defined by a rounded sidewall so as to define a round cavity. The medial and lateral sides of the channel are defined by a pair of deflectable flanges. The instrument system also includes a tibial base trial removeably coupled to the trial insert trial. The tibial base trial includes a plate configured to be positioned on a surgically-prepared proximal end of a patient's tibia. A post extends outwardly from a superior surface of the plate. The post is captured in the round cavity of the channel of the tibial bearing trial so as to allow the tibial bearing trial to rotate relative to the tibial base trial, but prevent movement of the tibial bearing trial in an inferior-superior direction relative to the tibial base trial.

In an embodiment, the tibial bearing trial includes a spine positioned between the pair of curved bearing surfaces.

The tibial bearing trial may further include an elongated slot formed in its superior surface. The elongated slot has a common longitudinal axis with the channel, is positioned superiorly of the channel, and opens into the channel. The post of the tibial base trial may have an annular-shaped flange extending outwardly therefrom, with such a flange of the post being captured in the slot.

In an embodiment, a posterior end of the slot is defined by the opening formed in the posterior section of the sidewall. The slot is wider than the diameter of the round cavity of the channel.

In an embodiment, each of the pair of deflectable flanges has a cam lobe formed therein, with the cam lobes extending inwardly into the channel toward one another.

The cam lobes may be separated from one another by a distance that is less than the diameter of the post of the tibial base trial.

In an embodiment, each of the deflectable flanges has an elongated cavity formed laterally adjacent thereto. A lateral edge of each of the deflectable flanges is urged into a corresponding one of the elongated cavities when the post of the tibial base trial contacts the cam lobes so as to urge the cam lobes away from one another.

The tibial bearing trial may be constructed of a polymeric material.

In another aspect, an orthopaedic surgical instrument includes a tibial bearing trial. The tibial bearing trial includes an inferior surface and a superior surface opposite the inferior surface. The superior surface has a pair of curved bearing surfaces formed therein. A spine is positioned between the pair of curved bearing surfaces, and a sidewall extends between the inferior surface and the superior surface. A channel is formed in the inferior surface, with a posterior end of the channel being defined by an opening formed in a posterior section of the sidewall. An anterior end of the channel is defined by a rounded sidewall so as to define a round cavity. The medial and lateral sides of the channel are defined by a pair of deflectable flanges.

The tibial bearing trial may further include an elongated slot formed in its inferior surface. The elongated slot has a common longitudinal axis with the channel. The elongated slot is positioned superiorly of the channel and opens into the channel.

In an embodiment, a posterior end of the slot is defined by the opening formed in the posterior section of the sidewall, with the slot being wider than the diameter of the round cavity of the channel.

In one embodiment, each of the pair of deflectable flanges has a cam lobe formed therein, with the cam lobes extending inwardly into the channel toward one another.

Each of the deflectable flanges has an elongated cavity formed laterally adjacent thereto. A lateral edge of each of the deflectable flanges is urged into a corresponding one of the elongated cavities when the cam lobes are contacted during installation of the tibial bearing trial onto a tibial base trial.

The tibial bearing trial may be constructed of a polymeric material.

In another aspect, a method of trialing an orthopaedic prosthetic assembly includes aligning a tibial bearing trial with a tibial base trial positioned on a proximal end of a patient's tibia, and thereafter advancing the tibial bearing trial in the anterior-to-posterior direction to move a post of the tibial base trial component into a posterior channel defined in the tibial bearing trial. The post of the tibial base trial is captured in the channel between a pair of deflectable flanges so as to snap-lock the tibial bearing trial to the tibial base trial such that the tibial bearing trial is permitted to rotate relative to the tibial base trial. Thereafter, the patient's joint is moved through a range of motion including extension and flexion to evaluate a configuration of the orthopaedic prosthetic assembly corresponding to the tibial base trial and the tibial bearing trial.

In an embodiment, the tibial bearing trial may be advanced in the posterior-to-anterior direction to detach the tibial bearing trial from tibial base trial. Thereafter, a second tibial bearing trial is selected that has a different size from the tibial bearing trial. Thereafter, the second tibial bearing trial is advanced in the anterior-to-posterior direction to move the post of the tibial base trial component into a posterior channel defined in the second tibial bearing trial. The post of the tibial base trial is then captured between a pair of deflectable flanges of the second tibial base trial so as to snap-lock the second tibial bearing trial to the tibial base trial such that the second tibial bearing trial is permitted to rotate relative to the tibial base trial. Thereafter, the patient's joint is moved through a range of motion including extension and flexion to evaluate a configuration of the orthopaedic prosthetic assembly corresponding to the tibial base trial and the tibial bearing trial.

In an embodiment, a cam lobe on each of the deflectable flanges is moved into contact with the post of the tibial base trial so as to urge the deflectable flanges laterally during advancement of the tibial bearing trial. The cam lobe on each of the deflectable flanges is moved out of contact with the post of the tibial base trial so as to allow the deflectable flanges to retract medially when the bearing trial snap-locks to the base trial.

In an embodiment, the tibial base trial has a substantially-planar superior surface, and the tibial bearing trial has a substantially-planar inferior surface. The posterior-most edge of the inferior surface of the tibial bearing trial remains in contact with the superior surface of the tibial base trial throughout advancement of the tibial bearing trial in the anterior-to-posterior direction to snap-lock the tibial bearing trial to the tibial base trial.

BRIEF DESCRIPTION

The detailed description particularly refers to the following figures, in which.

DETAILED DESCRIPTION

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
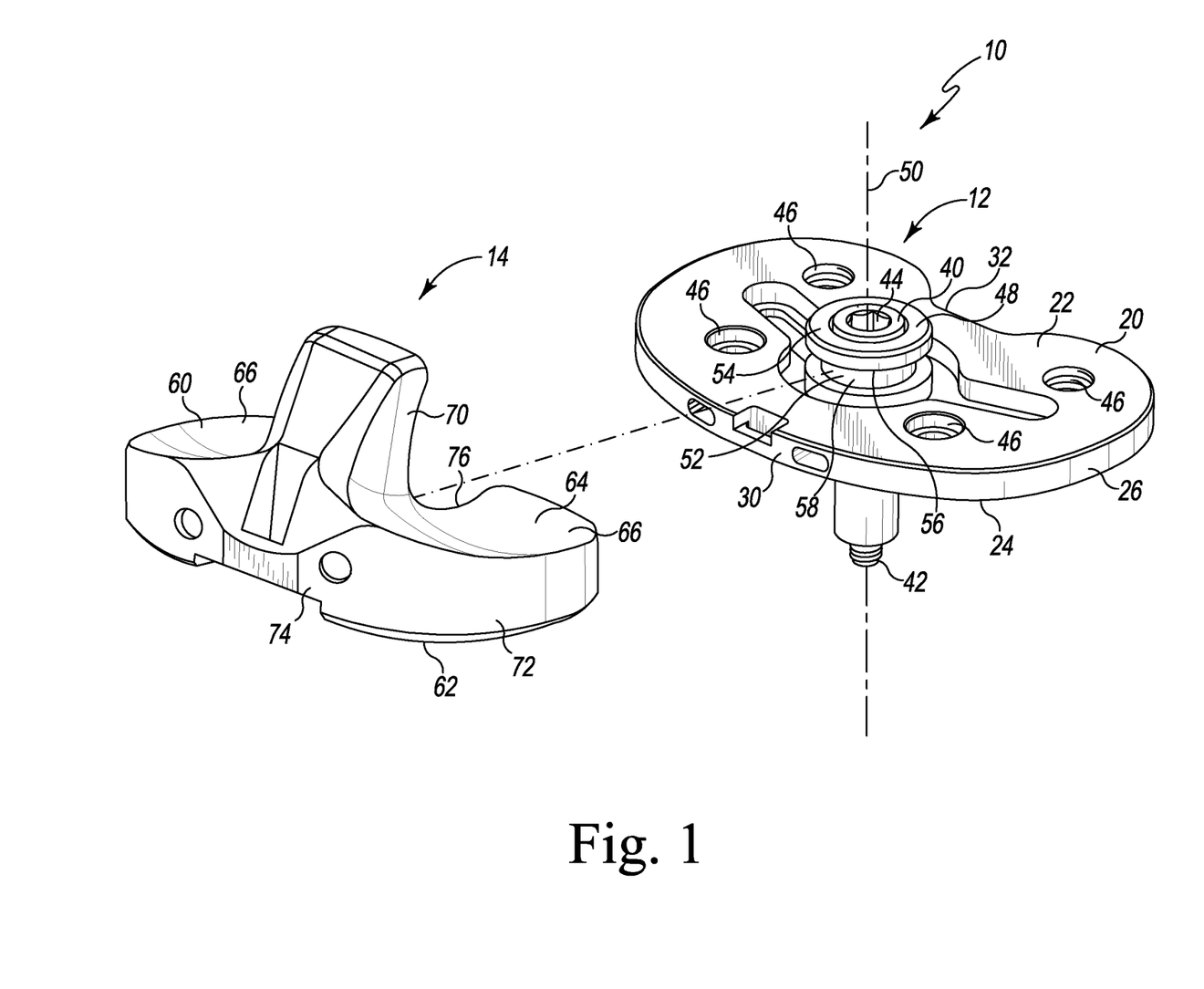
FIG. 1 is an exploded view of an orthopaedic surgical instrument system.

Referring now to FIG. 1, an orthopaedic surgical instrument system 10 includes a tibial base trial 12 and a tibial bearing trial 14 configured to be selectively coupled to the tibial base trial 12. The tibial base trial 12 and the tibial bearing trial 14 may be utilized with a femoral component (see FIG. 9) to size and select a tibial prosthesis for implantation into a patient's surgically-prepared tibia. In the illustrative embodiment, the femoral component may be a femoral trial component or a primary femoral component from a previous joint arthroplasty. It should be appreciated that the instrument system 10 may include a number of trial components 12, 14 of different sizes to accommodate a range of patient anatomies.

As described in greater detail below, the tibial bearing trial 14 is configured to be removably secured to the tibial base trial 12. During a surgical procedure, the surgeon may evaluate the range of motion of the patient's leg with the tibial bearing trial 14 positioned in the knee joint to assess, amongst other things, the range of motion and stability of the knee. The tibial bearing trial 14 is configured to be detached from the tibial base trial 12 during the surgical procedure and replaced with a tibial bearing trial of a different size to permit the surgeon to evaluate a range of possible implant sizes and select the one that provides the desired performance.

It should be appreciated that the tibial bearing component 14 is embodied as a "mobile tibial bearing trial." As used herein, such a term refers to a tibial bearing trial 14 that is permitted to rotate relative to the tibial base trial 12 when it is attached a tibial base trial component 14. In other words, a mobile tibial bearing trial is configured to rotate relative to the tibial base trial 12 in the anterior-posterior direction and/or the medial-lateral direction. In the illustrative embodiment described herein, the mobile bearing trial 14 is embodied as a revision trial.

The tibial base trial 12 is configured to be positioned on a surgically-prepared proximal end of a patient's tibia. In the illustrative embodiment, the base trial 12 includes a plate 20 shaped to be positioned on a proximal end of a patient's tibia. The plate 20 has a substantially-planar superior surface 22, an inferior surface 24, and an outer side wall 26 extending between the surfaces 22, 24. The outer side wall 26 has an anterior section 30 and a posterior section 32 shaped to match a proximal end of a resected tibia. In the illustrative embodiment, the anterior section 30 of the side wall 26 is convexly curved, and the posterior section 32 is concavely curved. It should be appreciated that the tibial base trial 12 may be formed in a number of different sizes to accommodate tibias of various sizes.

The tibial base trial 12 includes a captured locking bolt 40 extending in the superior-inferior direction. The locking bolt 40 has a threaded end 42 which extends downwardly from the inferior surface 24 of the plate 20. The threaded end 42 is sized to be received in a threaded bore (not shown) of a surgical instrument such as, for example, an elongated broach or stem trial component configured to be inserted in the intramedullary canal of the patient's tibia. The opposite end of the locking bolt 40 has a socket 44 formed therein. The socket 44 is configured to receive a hex-head driver (not shown). Rotation of the socket 44 with the hex-head driver causes rotation of the locking bolt's threaded end 42 thereby allowing the bolt 40, and hence the tibial base trial 12, to be secured to (and removed from) the elongated broach, stem trial, or other surgical instrument. The plate 20 also includes a number of fastener guides 46 configured to receive a fastener, such as a fixation pin (not shown), which may be utilized to secure the tibial base trial 12 to the surgically-prepared proximal end of the patient's tibia.

The tibial base trial 12 includes a post 48 that extends outwardly in the superior direction from the superior surface 22 of the plate 20 along a longitudinal axis 50. As will be described in more detail below, the post 48 is configured to secure the tibial bearing trial 14 to the tibial base trial 12. The post 48 includes a stem 52 extending superiorly from the superior surface 22 of the plate 20. An annular-shaped flange 54 extends outwardly from a distal end of the post 48. As such, the post's flange 54 has a larger diameter than its stem 52. An inferior surface 56 of the flange 54 faces the superior surface 22 of the plate 20. A groove 58 is defined between the inferior surface 56 of the flange 54 and the superior surface 22 of the plate 20. As described below, a locking mechanism of the tibial bearing trial 14 is configured to engage the stem 52 of the post 48 within the groove 58.

As described above, the tibial bearing trial 14 is configured to be selectively and removably coupled to the tibial base trial 12. As will be described in more detail below, the tibial bearing trial 14 may be anteriorly installed on, and uninstalled from, the tibial base trial 12 by moving it solely in the anterior-posterior direction without having to urge the tibial bearing trial 14 superiorly during either installation or detachment/removal thereof. As shown in FIG. 1, the tibial bearing trial 14 includes a body 60 having a substantially-planar inferior surface 62 and an opposite superior surface 64. The inferior surface 62 of the tibial bearing trial 14 is configured to abut the superior surface 22 of the plate 20 of the tibial base trial 12. The superior surface 64 of the tibial bearing trial 14 includes a pair of curved bearing surfaces 66 configured to correspond to the condylar surfaces of a femoral component (see FIG. 9). A spine 70 is positioned between the curved bearing surfaces 66 and extends superiorly from the superior surface 64 of the tibial bearing trial 14.

Figure 2:
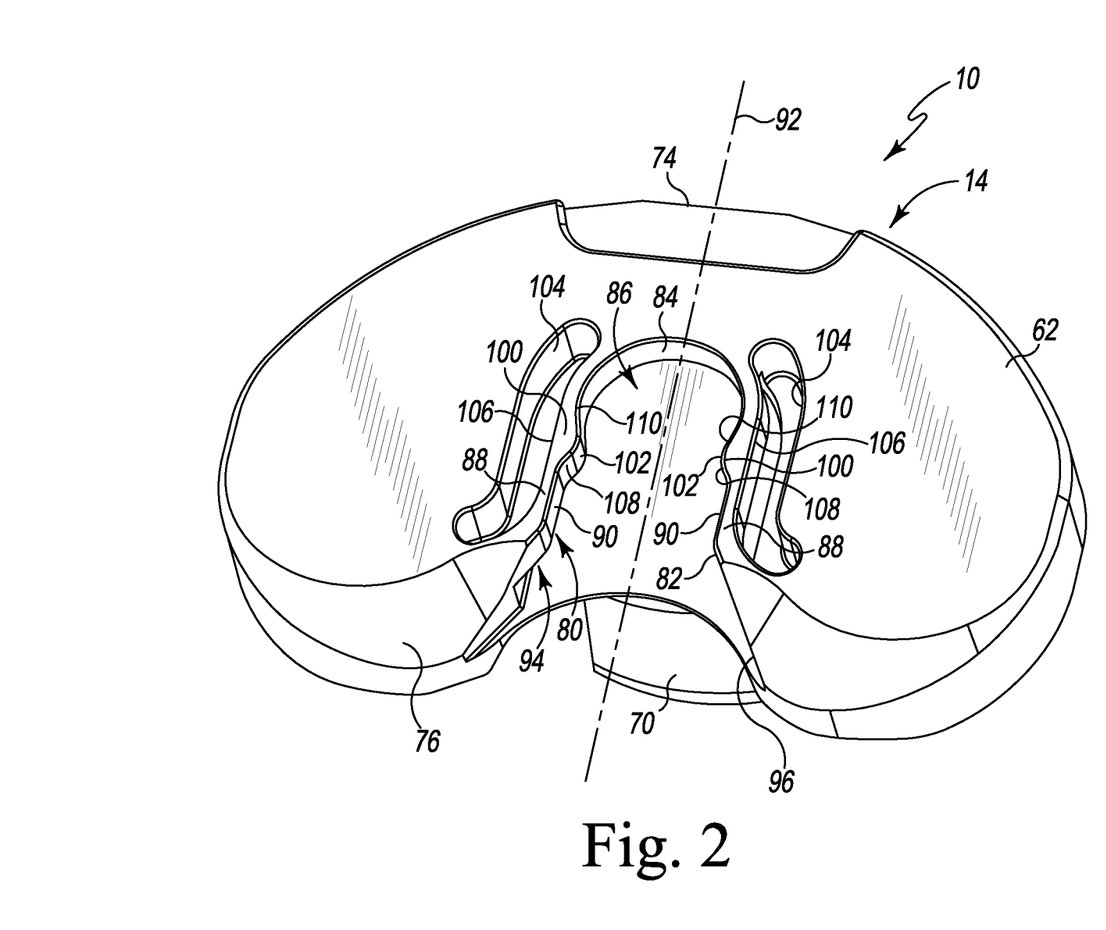
FIG. 2 is a bottom perspective view of the tibial bearing trial of the orthopaedic surgical instrument system of FIG. 1.
Figure 3:
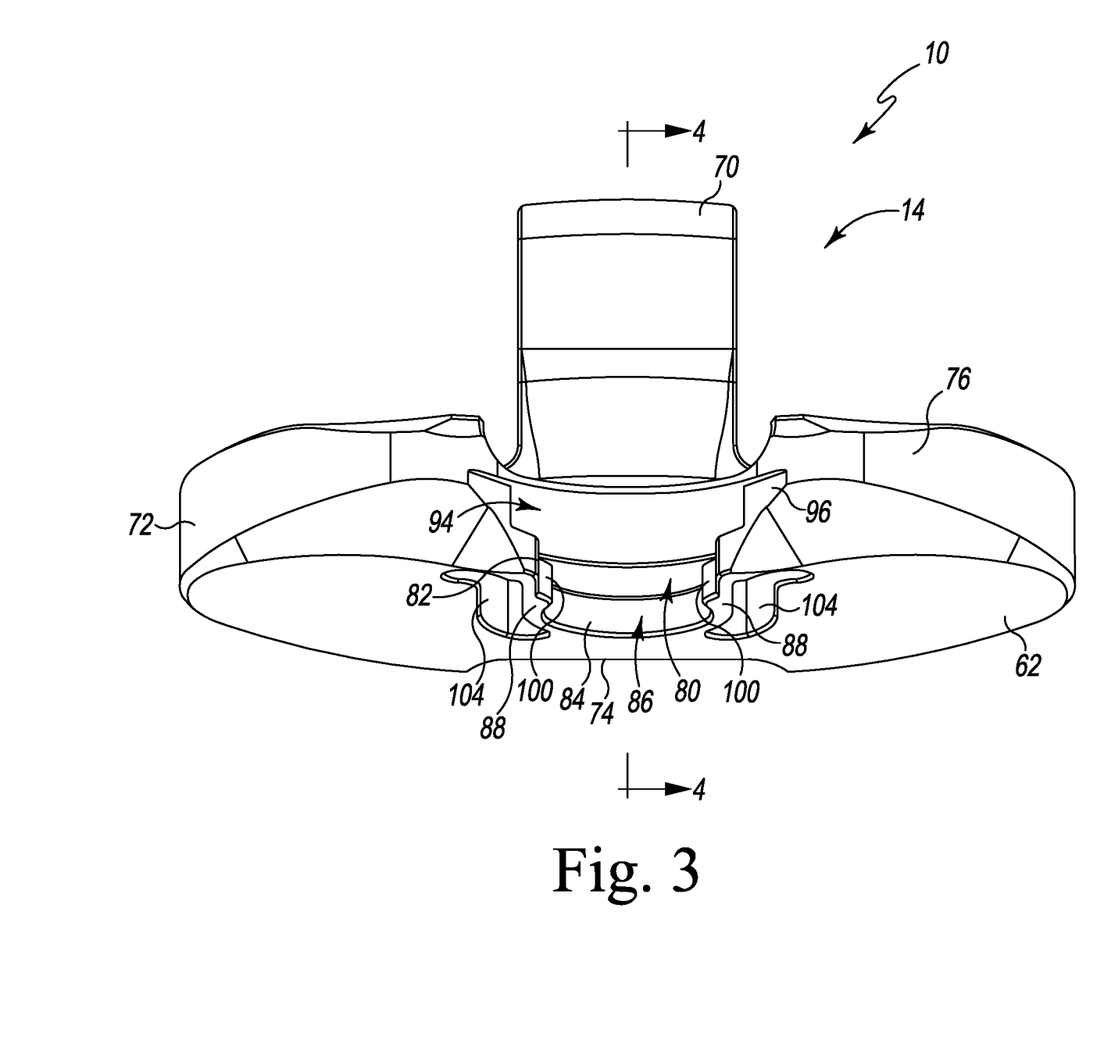
FIG. 3 is a rear perspective view of the tibial bearing trial of FIG. 2.
Figure 4:
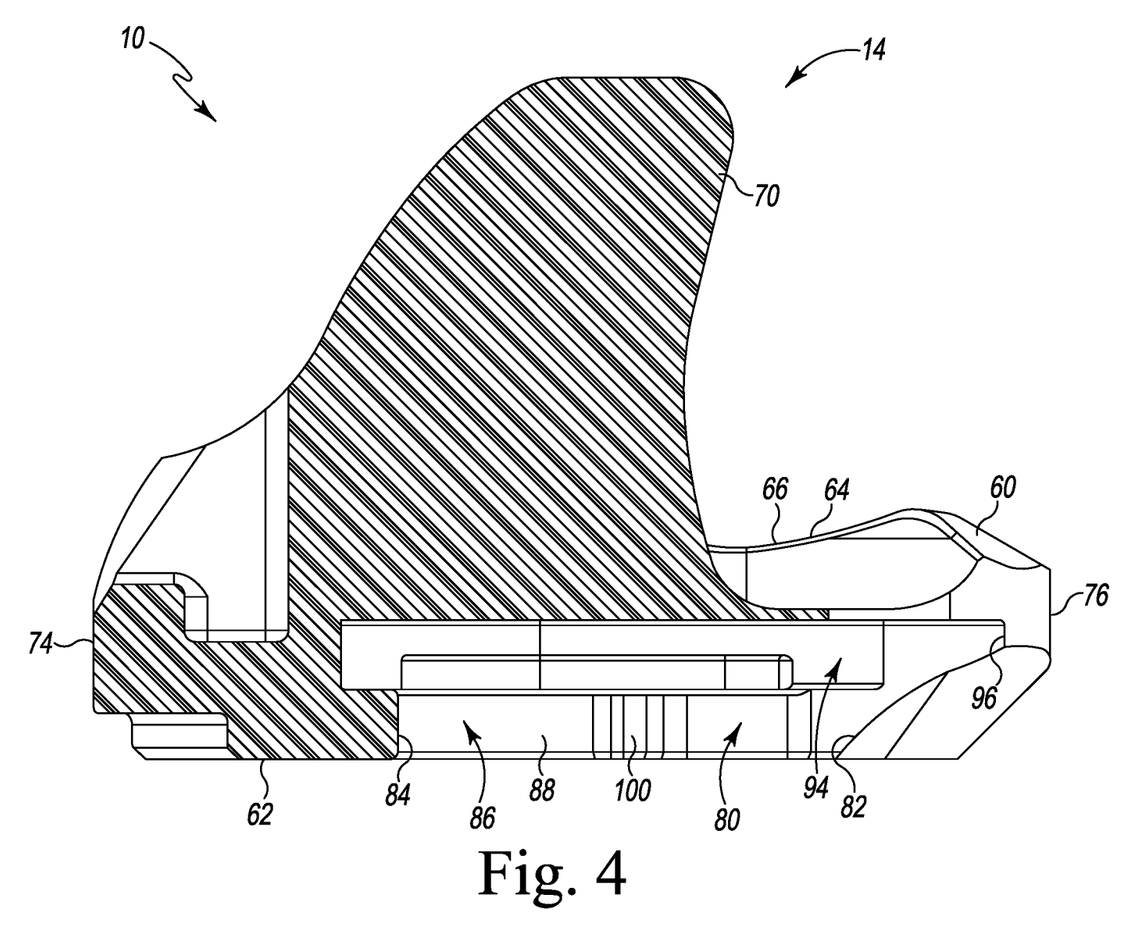
FIG. 4 is a cross-sectional view taken along the line 4-4 of FIG. 3, as viewed in the direction of the arrows.
Figure 5:
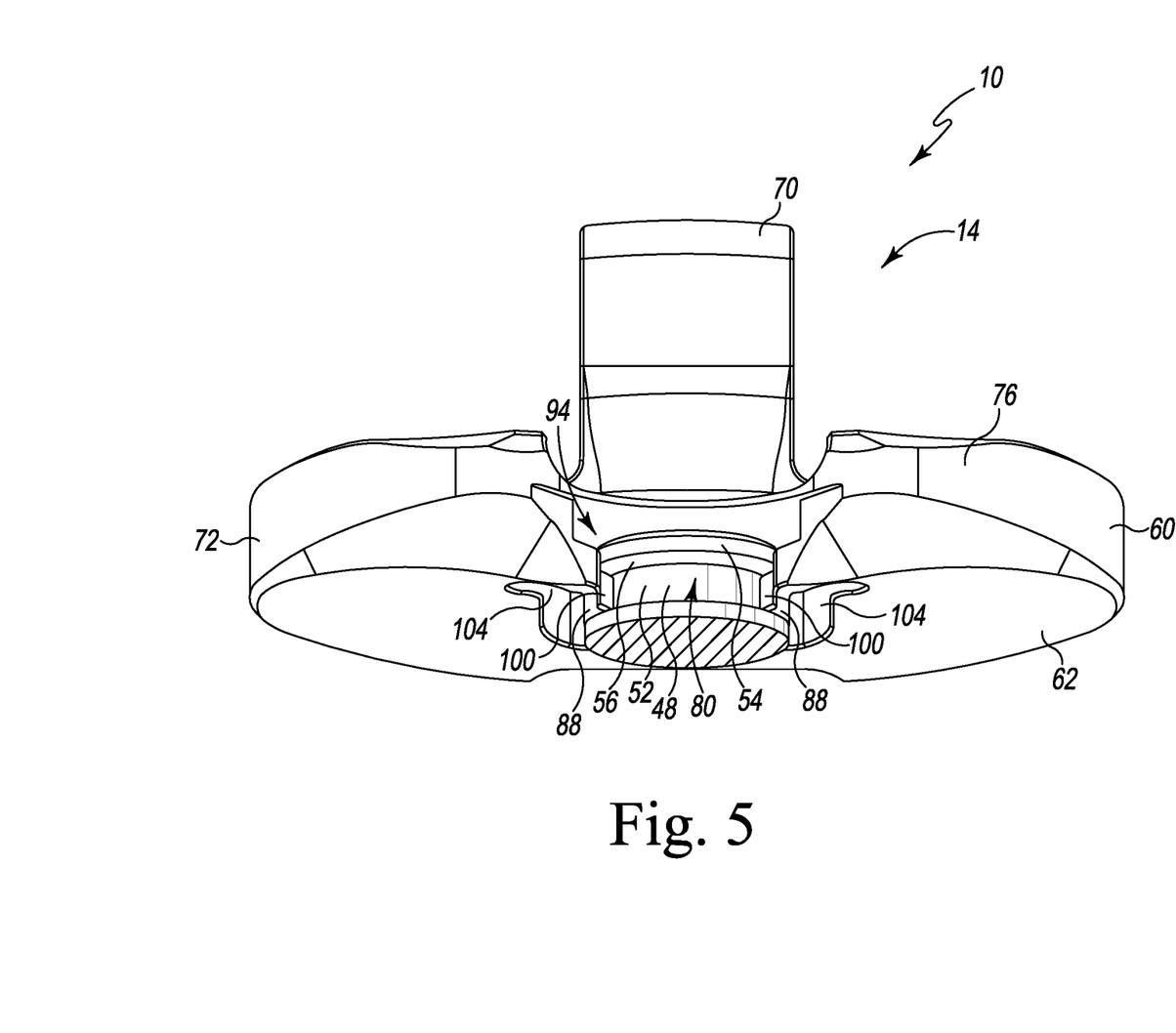
FIG. 5 is a view similar to FIG. 3, but showing the post of tibial base trial captured in the channel of the tibial bearing trial, note the post is shown in FIG. 5 cut away from tibial base trial for clarity of description.

The tibial bearing trial 14 includes an outer sidewall 72 having an anterior section 74 that is shaped to match the anterior section 30 of the tibial base trial 12 and a posterior section 76 that is shaped to match the posterior section 32 of the tibial base trial 12. Referring to FIGS. 2-4, a channel 80 is formed in the inferior surface 62 of the tibial bearing trial 14. The posterior end of the channel 80 is defined by an opening 82 formed in the posterior section 76 of the bearing trial's outer sidewall 72. The anterior end of the channel 80 is defined by a rounded sidewall 84. In such a way, the anterior end of the channel 80 defines a round cavity 86. As can be seen in FIG. 2, the inferior surface 62 of the tibial bearing trial 14 has a pair of deflectable flanges 88 formed therein. The medial and lateral sides of the channel 80 are defined by the medial edges 90 of the deflectable flanges 88. As can be seen in FIG. 2, the channel 80 extends in the anterior/posterior direction along a longitudinal axis 92. As such, the longitudinal axis 92 of the channel is orthogonal to the longitudinal axis 50 of the tibial base trial's post 48.

Figure 6:
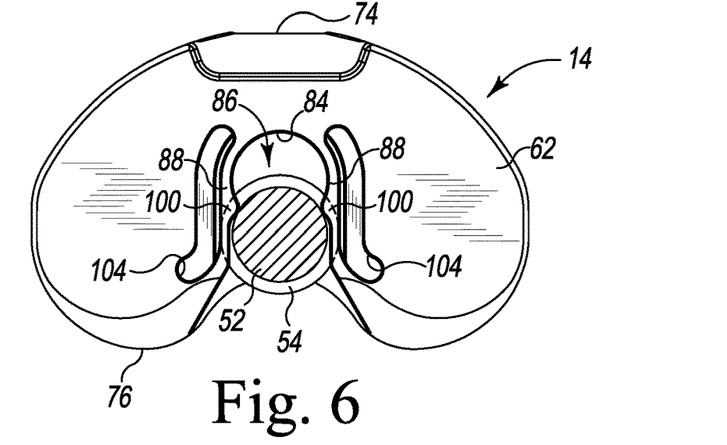
FIGS. 6-8 are diagrammatic bottom plan views of tibial bearing trial showing the post being captured in its channel so as to snap-lock the tibial bearing trial to the tibial base trial, note the post is shown cut away from tibial base trial for clarity of description in FIGS. 6-8.
Figure 7:
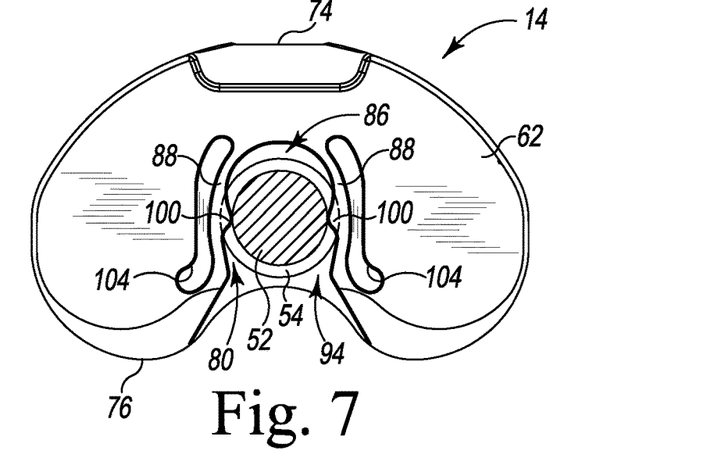
Figure 8:
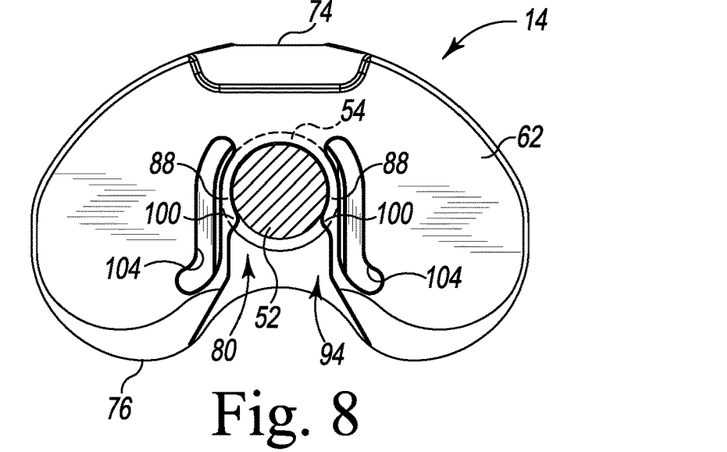

As can be seen in FIGS. 2-4, the inferior surface 62 of the tibial bearing trial 14 also has an elongated slot 94 formed therein. Like the channel 80, the posterior end of the slot 94 is defined by an opening 96 formed in the posterior section 76 of the bearing trial's outer sidewall 72. The slot 94 shares a common longitudinal axis with the channel 80 and, as such, extends in anteriorly away from the opening 96 in the anterior/posterior direction along the longitudinal axis 92. The slot 94 is positioned superiorly of the channel 80 and opens into it along its length. As can be seen in FIGS. 2-4, the slot 94 is wider that the channel 80, including the round cavity 86 defined in the channel's anterior end. As such, and as will be described in more detail below, the slot 94 is configured to receive the annular-shaped flange 54 of the post 48 as the post's stem 52 is received into channel 80 during installation of the tibial bearing trial 14 onto the tibial base trial 12. As will be discussed in more detail below in regard to FIGS. 6-8, the diameter of the annular-shaped flange 54 is greater than the width of the channel 80. As such, the tibial bearing trial 14 is prevented from lifting off the tibial base trial 12 (i.e., lifting superiorly off the tibial base trial 12) once the tibial bearing trial 14 is installed thereto.

As shown in FIG. 2, the medial edges 90 of each of the deflectable flanges 88 have a cam lobe 100 defined therein. The cam lobes 100 extend inwardly (i.e., medially) into the channel 80 toward one another. The tips 102 of the cam lobes 100 are separated from each other by a distance that is less than the diameter of the stem 52 of the post 48 of the tibial base trial 12. As such, during installation or detachment/removal of the tibial bearing trial 14, the stem 52 contacts the cam lobes 100 so as to deflect or otherwise urge the deflectable flanges 88 laterally away from one another. Specifically, as can be seen in FIG. 2, a pair of elongated cavities 104 is formed in the inferior surface 62 of the tibial bearing trial 14. The cavities 104 are positioned laterally adjacent to the lateral edges 106 of the deflectable flanges 88. In such an arrangement, the lateral edges 106 of the deflectable flanges 88 define the medial sides of the cavity 104 adjacent to it.

As can be seen in FIGS. 5-8, during installation of the tibial bearing trial 14 onto the tibial base trial 12, the stem 52 of the base trial's post 48 is advanced into the channel 80 through the opening 82 formed in the posterior section 76 of the bearing trial's outer sidewall 72 while the annular-shaped flange 54 of the base trial's post 48 enters the slot 94 through the opening 96 formed in the posterior section 76 of the bearing trial's outer sidewall 72. As the tibial bearing trial 14 continues to be moved in the anterior-to-posterior direction, the outer surface of the stem 52 of the base trial's post 48 advances into contact with the posterior cam surfaces 108 of the cam lobes 100 thereby causing the deflectable flanges 88 to deflect or otherwise be urged laterally away from one another. The deflectable flanges 88 continue to deflect as the stem 52 rides up the posterior cam surfaces 108. Once the stem 52 passes the tips 102 of the cam lobes 100, the stem 52 begins to ride down the anterior cam surfaces 110 of the cam lobes 100 thereby allowing the deflectable flanges 88 to move medially back toward one another. Once the stem 52 clears the anterior cam surfaces 110, the deflectable flanges 88 are retracted/returned to their original positions thereby capturing the stem 52 of the base trial's post 48 in the round cavity 86 of the channel 80 so as to snap-lock the tibial bearing trial 14 to the tibial base trial 12.

To detach the tibial bearing trial 14 to the tibial base trial 12, the bearing trial 14 is pulled or otherwise advanced in the posterior-to-anterior direction relative to the base trial 12. Doing so causes the outer surface of the stem 52 of the base trial's post 48 to be advanced into contact with the anterior cam surfaces 110 of the cam lobes 100 thereby causing the deflectable flanges 88 to deflect or otherwise be urged laterally away from one another. The deflectable flanges 88 continue to deflect as the stem 52 rides up the anterior cam surfaces 110. Once the stem 52 passes the tips 102 of the cam lobes 100, the stem 52 begins to ride down the posterior cam surfaces 108 of the cam lobes 100 thereby allowing the deflectable flanges 88 to move medially back toward one another. Once the stem 52 clears the posterior cam surfaces 108, the deflectable flanges 88 are retracted/returned to their original positions thereby allowing the stem 52 of the base trial's post 48 to be advanced out of the channel 80 through the opening 82 formed in the posterior section 76 of the bearing trial's outer sidewall 72 while the annular-shaped flange 54 of the base trial's post 48 exits the slot 94 through the opening 96 formed in the posterior section 76 of the bearing trial's outer sidewall 72 so as to detach the tibial bearing trial 14 from the tibial base trial 12.

The illustrated tibial bearing trial 14 is one of a plurality of tibial bearing trials that make a multi-piece system configured to assist the surgeon in selecting a size and configuration of the implanted tibial bearing component. As such, the surgeon is able to assemble a tibial bearing trial 14 of one size and configuration, evaluate the performance of that tibial bearing trial 14, and then replace it with a different tibial bearing trial 14 as necessary to determine intraoperatively the type and configuration of the tibial bearing component to be implanted.

The tibial base trial 12 is illustratively formed from a metallic material such as cobalt-chromium or titanium, but may be formed from other materials, such as a ceramic material, a polymer material, a bio-engineered material, or the like. The tibial bearing trial 14 is illustratively formed from a polymer material such as an ultra-high molecular weight polyethylene (UHMWPE), but may be formed from other materials, such as a ceramic material, a metallic material, a bio-engineered material, or the like.

Figure 9:
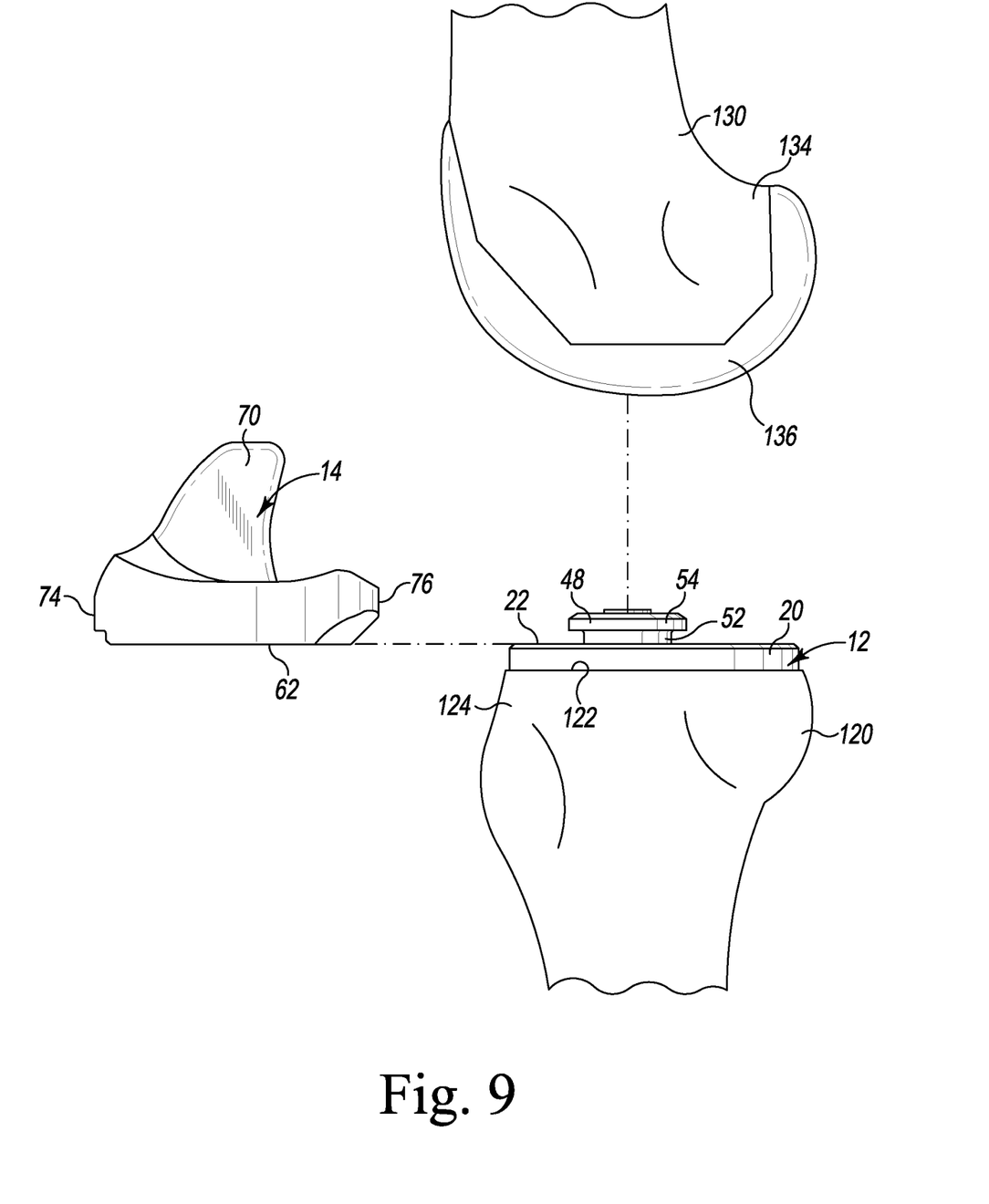
FIG. 9 is an exploded perspective view showing the tibial base trial positioned on the surgically-prepared proximal end of a patient's tibia with the tibial bearing trial being installed there.

Referring now to FIG. 9, a surgeon may use the orthopaedic surgical instrument system 10 during the trialing process of a surgical procedure to implant a knee prosthesis. To do so, the surgeon initially resects or otherwise surgically-prepares the patient's tibia 120 to form a smooth planar surface 122 on a proximal end 124 of the tibia 120. The surgeon then installs the tibial base trial 12 on the resected planar surface 122 of the patient's tibia 120. If needed, the surgeon may also perform a resection of the distal end 134 of the patient's femur 130 to surgically prepare the femur to receive a femoral trial 136 for use in a trial reduction procedure. In an embodiment in which a primary femoral component (not shown) from a previous joint arthroplasty is not being replaced, the surgeon may trial the tibial bearing trial 14 with the primary femoral component.

Once the tibial base trial 12 has been installed on the resected planar surface 122 of the patient's tibia 120, the surgeon installs the tibial bearing trial 14 to the base trial 12 from the anterior side of the patient's tibia 120. To do so, the tibial bearing trial 14 is first aligned with the tibial base trial 12 such that the posterior-most edge of the inferior surface 62 of the bearing trial 14 is positioned on the superior surface 22 on the anterior portion of the base trial's plate 20. The tibial bearing trial 14 is then advanced onto the tibial base trial 12 in the anterior-to-posterior direction such that the stem 52 of the base trial's post 48 is advanced into the channel 80 through the opening 82 formed in the posterior section 76 of the bearing trial's outer sidewall 72 while the annular-shaped flange 54 of the base trial's post 48 enters the slot 94 through the opening 96 formed in the posterior section 76 of the bearing trial's outer sidewall 72. As the tibial bearing trial 14 continues to be moved in the anterior-to-posterior direction, the stem 52 of the base trial's post 48 advances into contact with the cam lobes 100 of the bearing's trial's deflectable flanges 88 thereby causing the deflectable flanges 88 to initially deflect to allow the stem 52 to pass and thereafter retract back into their original positions thereby capturing the stem 52 of the base trial's post 48 in the round cavity 86 of the channel 80 so as to snap-lock the tibial bearing trial 14 to the tibial base trial 12.

It should be appreciated that during such installation of the tibial bearing trial 14, the bearing trial 14 is advanced solely in the anterior-to-posterior direction without having to be urged superiorly in any amount whatsoever. Specifically, the posterior-most edge of the bearing trial's inferior surface 62 remains in contact with the superior surface 22 of the base trial's plate 20 throughout installation of the tibial bearing trial 14.

It should be appreciated that when installed on the tibial base trial 12, the stem 52 and the annular-shaped flange 54 of the base trial's post are positioned in the rounded anterior ends of the bearing trial's channel 80 and slot 94, respectively. As such, the tibial bearing trial 14 is free to rotate relative to the tibial base trial 12 when its snap-locked thereto. However, because the diameter of the annular-shaped flange 54 of the base trial's post 48 is larger than the width of the channel 80, the deflectable flanges 88 of the tibial bearing trial 14 are captured in the groove 58 defined between the inferior surface 56 of the flange 54 and the superior surface 22 of the plate 20. As such, while tibial bearing trial 14 is free to rotate relative to the tibial base trial 12, it is prevented from lifting off of base trial 12. That is, the tibial bearing trial 14 is prevented from moving in the inferior-superior direction when it is snap-locked to the tibial base trial 12.

Once the tibial bearing trial 14 is snap-locked to the tibial base trial 12, the surgeon may perform an initial trial reduction with the instrument system 10. In doing so, the surgeon uses the instrument system 10 to evaluate the stability and kinematics of the patient's femur 130 and tibia 120. To do so, the surgeon moves the patient's tibia 120 relative to the patient's femur 130 between full flexion and full extension. During such movement of the patient's knee, the surgeon evaluates the articulation of the femoral trial 136 (or the primary femoral component (not shown) from a previous joint arthroplasty if it is not being replaced) and the tibial bearing trial 14 to determine, amongst other things, desired contact points between the two trials, range of motion, and cam/spine engagement.

If the surgeon desires to try a different size or configuration of the tibial bearing trial 14, the surgeon detaches the installed bearing trial 14 by pulling or otherwise advancing the bearing trial 14 in the posterior-to-anterior direction relative to the base trial 12. Doing so causes the stem 52 of the base trial's post 48 to be advanced into contact with the cam lobes 100 thereby causing the deflectable flanges 88 to initially deflect to allow the stem 52 to pass and thereafter retract back into their original positions thereby allowing the stem 52 of the base trial's post 48 to be advanced out of the channel 80 through the opening 82 formed in the posterior section 76 of the bearing trial's outer sidewall 72 while the annular-shaped flange 54 of the base trial's post 48 exits the slot 94 through the opening 96 formed in the posterior section 76 of the bearing trial's outer sidewall 72 so as to detach the tibial bearing trial 14 from the tibial base trial 12.

Thereafter, the surgeon may install a different tibial bearing trial 14 on the tibial base trial 12 in the manner described above. With the second tibial bearing trial 14 installed, the surgeon may then perform a subsequent trial reduction in the manner described above.

Once the desired size and configuration of the tibial base trial 12 and the tibial bearing trial 14 have been determined by the surgeon, the trials 12, 14 are removed from the patient's tibia 12 and the corresponding implant components are implanted in the patient's tibia 12.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument system, comprising:
    a tibial bearing trial including (i) an inferior surface, (ii) a superior surface opposite the inferior surface and having a pair of curved bearing surfaces formed therein, (iii) a sidewall extending between the inferior surface and the superior surface, and (iv) a channel formed in the inferior surface, wherein (a) a posterior end of the channel is defined by an opening formed in a posterior section of the sidewall, (b) an anterior end of the channel is defined by a rounded sidewall so as to define a round cavity, and (c) medial and lateral sides of the channel are defined by a pair of deflectable flanges, and
    a tibial base trial removeably coupled to tibial bearing trial, the tibial base trial including (i) a plate configured to be positioned on a surgically-prepared proximal end of a patient's tibia, and (ii) a post extending outwardly from a superior surface of the plate, wherein the post is captured in the round cavity of the channel of the tibial bearing trial so as to allow the tibial bearing trial to rotate relative to the tibial base trial, but prevent movement of the tibial bearing trial in an inferior-superior direction relative to the tibial base trial.

2. The orthopaedic surgical instrument system of claim 1, wherein the tibial bearing trial includes a spine positioned between the pair of curved bearing surfaces.

3. The orthopaedic surgical instrument system of claim 1, wherein:
    the tibial bearing trial further includes an elongated slot formed therein, the elongated slot having a common longitudinal axis with the channel,
    the elongated slot is positioned superiorly of the channel and opens into the channel,
    the post of the tibial base trial has an annular-shaped flange extending outwardly therefrom, and
    the flange of the post is captured in the slot.

4. The orthopaedic surgical instrument system of claim 3, wherein:
    the opening formed in the posterior section of the sidewall defines a posterior end of the slot, and
    the width of the slot is greater than the diameter of the round cavity of the channel.

5. The orthopaedic surgical instrument system of claim 1, wherein:
    each of the pair of deflectable flanges has a cam lobe formed therein, and
    the cam lobes extend inwardly into the channel toward one another.

6. The orthopaedic surgical instrument system of claim 5, wherein the cam lobes are separated from one another by a distance that is less than the diameter of the post of the tibial base trial.

7. The orthopaedic surgical instrument system of claim 5, wherein:
    each of the deflectable flanges has an elongated cavity formed laterally adjacent thereto, and
    a lateral edge of each of the deflectable flanges is urged into a corresponding one of the elongated cavities when the post of the tibial base trial contacts the cam lobes so as to urge the cam lobes away from one another.

8. The orthopaedic surgical instrument system of claim 1, wherein the tibial bearing trial is constructed of a polymeric material.

9. An orthopaedic surgical instrument, comprising:
    a tibial bearing trial, comprising:
        an inferior surface,
        a superior surface opposite the inferior surface and having a pair of curved bearing surfaces formed therein,
        a spine positioned between the pair of curved bearing surfaces,
        a sidewall extending between the inferior surface and the superior surface, and
        a channel formed in the inferior surface, wherein (i) a posterior end of the channel is defined by an opening formed in a posterior section of the sidewall, (ii) an anterior end of the channel is defined by a rounded sidewall so as to define a round cavity, (iii) medial and lateral sides of the channel are defined by a pair of deflectable flanges, (iv) each of the pair of deflectable flanges has a cam lobe formed therein, and (v) the cam lobes extend inwardly into the channel toward one another.

10. The orthopaedic surgical instrument of claim 9, wherein:
    the tibial bearing trial further includes an elongated slot formed therein, the elongated slot having a common longitudinal axis with the channel, and
    the elongated slot is positioned superiorly of the channel and opens into the channel.

11. The orthopaedic surgical instrument of claim 10, wherein:
the opening formed in the posterior section of the sidewall defines a posterior end of the slot, and
the width of the slot is greater than the diameter of the round cavity of the channel.

12. The orthopaedic surgical instrument of claim 9, wherein:
each of the deflectable flanges has an elongated cavity formed laterally adjacent thereto, and
a lateral edge of each of the deflectable flanges is urged into a corresponding one of the elongated cavities when the cam lobes are contacted during installation of the tibial bearing trial onto a tibial base trial.

13. The orthopaedic surgical instrument of claim 9, wherein the tibial bearing trial is constructed of a polymeric material.

14. A method of trialing an orthopaedic prosthetic assembly, the method comprising:
aligning a tibial bearing trial with a tibial base trial positioned on a proximal end of a patient's tibia,
advancing the tibial bearing trial in the anterior-to-posterior direction to move a post of the tibial base trial component into a posterior channel defined in the tibial bearing trial,
capturing the post of the tibial base trial in the channel between a pair of deflectable flanges so as to snap-lock the tibial bearing trial to the tibial base trial such that the tibial bearing trial is permitted to rotate relative to the tibial base trial, and
moving the patient's joint through a range of motion including extension and flexion to evaluate a configuration of the orthopaedic prosthetic assembly corresponding to the tibial base trial and the tibial bearing trial.

15. The method of claim 14, further comprising:
advancing the tibial bearing trial in the posterior-to-anterior direction to detach the tibial bearing trial from tibial base trial,
selecting a second tibial bearing trial having a different size from the tibial bearing trial,
advancing the second tibial bearing trial in the anterior-to-posterior direction to move the post of the tibial base trial component into a posterior channel defined in the second tibial bearing trial,
capturing the post of the tibial base trial between a pair of deflectable flanges of the second tibial base trial so as to snap-lock the second tibial bearing trial to the tibial base trial such that the second tibial bearing trial is permitted to rotate relative to the tibial base trial, and
moving the patient's joint through a range of motion including extension and flexion to evaluate a configuration of the orthopaedic prosthetic assembly corresponding to the tibial base trial and the tibial bearing trial.

16. The method of claim 14, wherein:
advancing the tibial bearing trial comprises moving a cam lobe on each of the deflectable flanges into contact with the post of the tibial base trial so as to urge the deflectable flanges laterally, and
capturing the post of the tibial base trial comprises moving the cam lobe on each of the deflectable flanges out of contact with the post of the tibial base trial so as to allow the deflectable flanges to retract medially.

17. The method of claim 14, wherein:
the tibial base trial has a substantially-planar superior surface,
the tibial bearing trial has a substantially-planar inferior surface, and
the posterior-most edge of the inferior surface of the tibial bearing trial remains in contact with the superior surface of the tibial base trial throughout advancement of the tibial bearing trial in the anterior-to-posterior direction to snap-lock the tibial bearing trial to the tibial base trial.

* * * * *